United States Patent [19]
Greenwood

[11] Patent Number: 5,120,314
[45] Date of Patent: Jun. 9, 1992

[54] SINGLE USE HYPODERMIC SYRINGE

[76] Inventor: Eugene C. Greenwood, 2956 Peppertree La., Apt. B, Costa Mesa, Calif. 92626

[21] Appl. No.: 673,951

[22] Filed: Mar. 22, 1991

[51] Int. Cl.⁵ .............................................. A61M 5/00
[52] U.S. Cl. ...................................... 604/110; 604/220
[58] Field of Search ............... 604/110, 218, 220, 111, 604/187

[56] References Cited

U.S. PATENT DOCUMENTS

| | | | |
|---|---|---|---|
| 4,713,056 | 12/1987 | Butterfield | 604/110 |
| 4,986,812 | 1/1991 | Perler | 604/220 |
| 5,000,737 | 3/1991 | Free et al. | 604/218 X |
| 5,021,047 | 6/1991 | Movern | 604/110 |

Primary Examiner—John D. Yasko

[57] ABSTRACT

A single use hypodermic syringe uses a generally cylindrical elongated syringe body defining a center bore and supporting a hollow needle in communication with the center bore through the inlet/output channel. A movable piston formed of an elastic material is sealingly supported within the syringe bore. A piston driver member extends into the syringe bore and is coupled to the piston. An annulus ring is fixed within the center bore near the inlet/outlet channel. The annulus permits the piston to pass over it when delivering an injection but locks onto the piston at the completion of the injection, precluding any further use of the syringe.

14 Claims, 4 Drawing Sheets

SINGLE USE HYPODERMIC SYRINGE

FIELD OF THE INVENTION

This invention relates generally to hypodermic syringes and particularly to a single use syringe incapable of multiple use.

BACKGROUND—CROSS REFERENCE TO RELATED APPLICATIONS

The present invention relates to standard plastic hypodermic syringes. The inventor of the present invention has been a participant in two related patents, U.S. Pat. Nos. 4,923,443 and 4,950,240 in which a connection between the piston and piston driver is broken or cut when the piston is driven forward to deliver the injection, thus preventing the syringe from being used to give a second injection. Although the object of the previous inventions is the same as the present invention, the present invention bears virtually no actual resemblance to the patents listed above.

BACKGROUND OF THE INVENTION

The present invention relates to standard plastic hypodermic syringes. Although the standard disposable hypodermic syringe is intended to be used once and discarded, it is possible to use the syringe many times. When a standard hypodermic syringe falls into the hands of drug addicts, it is frequently used by two or more addicts to give multiple injections without sterilizing, thereby transfering any infectious disease one might have to the other. This practice has led to a serious increase in AIDS cases.

Many attempts have been made to invent a hypodermic syringe which could be used only once. As an example, Wozniak et al. in U.S. Pat. No. 4,781,683 teaches a single use syringe which is automatically rendered inoperative when a fluid containing water is drawn into the syringe. This is accomplished by incorporating a hydrophilic insert into the internal wall of the syringe body at the narrow inlet/outlet channel of the syringe. When this insert is contacted by a fluid containing water, it absorbs some of the water and swells in size, closing off the passage.

An additional single use syringe is taught by Trenner in U.S. Pat. No. 4,781,684 in which an annular groove is provided near the discharge end of the syringe barrel which has a diameter greater than the interior diameter of the barrel. A locking element located between the piston and piston driver has an outside diameter which is greater than the inside diameter of the barrel. When the fluid is fully expelled from the syringe, the locking element engages the annular groove, preventing withdrawal of the piston.

Another single use hypodermic syringe is taught by Kosinski in U.S. Pat. No. 4,961,728. Kosinski inserts a locking element between the syringe barrel and the piston driver, positioned between the specially constructed structural flutes of the piston driver. As the piston driver moves in a distal direction, the barbs of the locking element slide along the inside surface of the barrel, but when there is proximal movement, the barbs dig in and prevent movement of the piston driver in the proximal direction, thereby preventing its use in giving a second injection.

While the foregoing described prior art devices provide some protection and increased safety of the use of the hypodermic syringe and some protection of the reuse thereof, they always render the hypodermic syringe much more costly to manufacture and more cumbersome to use.

There remains, therefore, a need in the art for a convenient to use, inexpensive to manufacture hypodermic syringe which is limited to a single use. Additionally, there remains the need for an inexpensive device which can be added to any existing hypodermic syringe which will make it into a single use syringe.

SUMMARY OF THE INVENTION

Accordingly, it is the object of the present invention to provide an improved hypodermic syringe. It is a more particular object of the present invention to provide an improved hypodermic syringe designed for a single use. It is a still more particular object of the present invention to provide an improved hypodermic syringe for single use which is automatically rendered inoperable following its first use. In addition, it is a particular object of the present invention to provide an improved hypodermic syringe which requires no dimensional modification of the basic parts of the standard disposable hypodermic syringe, permitting only a slight increase in manufacturing cost and scheduling. It is a further particular object of the present invention to provide an improved hypodermic syringe in which an off-the-shelf syringe can be automatically rendered incapable of giving a second injection by the addition of a simple auxiliary part.

In accordance, there is provided a metal annulus which is positioned within the interior front of the barrel of a standard hypodermic syringe which allows usage as a standard hypodermic syringe but when the hypodermic syringe is activated to a closed position completing the first injection, the annulus automatically locks onto the piston or piston driver, preventing the syringe from being reused to give another injection.

For the purpose of the description of the present invention, the term "distal end" refers to the end farther from the person holding the syringe in the inject position and the term "proximal end" refers to the end closer to the holder of the syringe.

A standard hypodermic syringe assembly has a cylindrical barrel having an inside surface describing a chamber for containing fluid, an open barrel end, and a distal barrel end having a narrow passageway which communicates with the hollow needle. A piston driver having a proximal and a distal end moves within the barrel. The distal end of the piston driver is attached to the proximal end of an elastic piston which is slidably positioned in fluid tight engagement in the barrel. Abutting the proximal end of the piston, the piston driver has a face which pushes on the piston when driving the piston toward the distal end of the syringe barrel. The piston driver also has an attachment inside the piston for pulling the piston in the proximal direction. The proximal end of the piston driver extends out through the open end of the syringe barrel and end with a flange which can be grasped with the fingers and/or thumb for the purpose of drawing fluid through the needle and into the barrel and for then forcing the fluid out through the needle.

Into this standard hypodermic syringe, close fitting to the inside wall of the barrel, the present invention places a thin, hard cylindrical annulus of narrow axial width at the distal end of the syringe barrel. The annulus has one or more outward facing sharp edged flexible projections which face in the proximal direction and are angled so that when being placed in the syringe barrel they can slide into the barrel from the proximal end to the distal end but will dig into the inside of the barrel and lock against any attemped movement in the opposite direction. Another part of the annulus is one or more inwardly facing projections which are angled such that the elastic piston will easily pass over them when moving in the distal direction to the distal end of the barrel when giving an injection, but the inward facing projections will lock onto the piston and prevent its movement relative to the annulus when the piston is attemped to be moved in the proximal direction after giving the injection. Thus, with the annulus locked against the inside wall of the barrel in a manner which prevents proximal movement and the piston locked against proximal movement by the annulus, motion of the piston in the proximal direction relative to the barrel is prevented, precluding the use of the syringe in giving a second injection.

Another feature of the present invention is means which allow the annulus to be compressed or expanded in diameter, thus making it possible to adapt to variations in the barrel inside diameter.

Another embodiment of the present invention in a standard disposable hypodermic syringe assembly is a thin, hard annulus similar to that described above, but which is bonded in place near the distal end of the inside of the syringe barrel instead of being locked by the proximal outward facing projections.

An advantage of the narrow axial width of the annulus is that it presents only a slight obstruction to the view through the syringe barrel of the fluid within.

Another advantage in the construction of the annulus is its thin material thickness which, when placed in a standard hypodermic syringe, displaces only a very small volume within the fluid containment chamber in the syringe. Naturally, in syringes originally manufactured with the annulus in place, the volume marking label can be modified to correct for the reduced volume due to the annulus.

In a product whose production quantities number in the millions of units per day, being able to insert the annulus into a standard hypodermic syringe without modification of the syringe and the molds for their manufacture is a major advantage in cost conservation. This also contributes greatly to the speed and simplicity of conversion to the single use mode.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENTS

Figure 1:
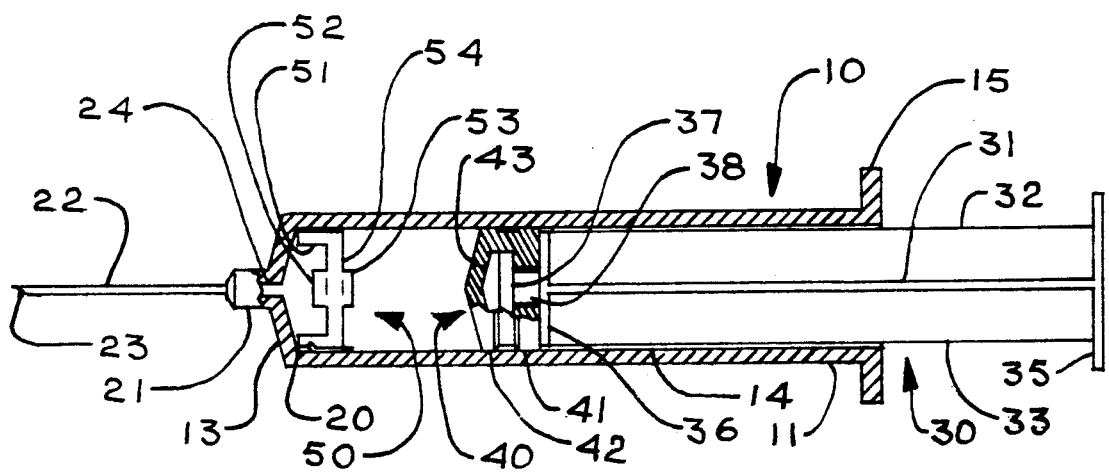
FIG. 1 sets forth a partially sectioned side view of a hypodermic syringe in the partially opened position constructed in accordance with the present invention.

FIG. 1 sets forth a partial section view of a hypodermic syringe 10 constructed in accordance with the present invention. Syringe 10 includes an elongated generally cylindrical syringe body 11 defining a flange 15 at one end and a taper 13 at the other end. Syringe body 11 further defines an interior generally cylindrical syringe bore 14 extending from flange 15 to a funnel end 20. A needle retainer 21 is formed at the distal end of syringe body 11 proximate taper 13 and in turn supports an elongated hollow needle 22 defining a point 23. A passage 24 defined within syringe body 11 extends from funnel end 20 to needle retainer 21 and provides communication between needle 22 and bore 14.

A piston driver 30 is formed of a quartet of outwardly extending rib members 31, 32, 33 and 34 (The latter not shown). Ribs 31 through 34 are commonly joined and generally perpendicularly arranged to provide an elongated rigid member capable of supporting substantial tension and compression forces. Piston driver 30 further defines a gripping flange 35 and a piston pushing flange 36 at opposite ends of ribs 31 through 34. A generally planar cylindrical retractor flange 37 is joined to retractor shaft 38 within cavity 43 of piston 40, captivating piston 40 on the distal end of piston driver 30. Syringe body 11 and piston driver 30 are molded from a plastic material such as polypropylene.

Piston 40, formed of a resilient elastic material such as rubber, defines a pair of outwardly extending entending sealing lobes 41 and 42 which form fluid tight contact with the interior of bore 14. Piston 40 further defines an interior cavity 43.

Within syringe bore 14 at funnel end 20 and in slidable close contact with syringe bore 14 is annulus 50, made of a hard, thin material such as stainless steel.

Figure 2:
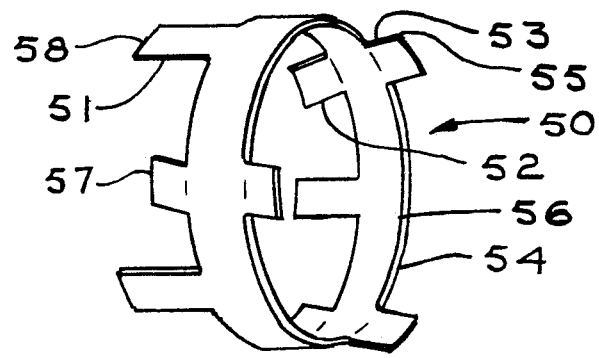
FIG. 2 sets forth a view of the annulus of the present invention.

FIG. 2 sets forth a view of annulus 50 constructed in accordance with the present invention. A typical material for annulus 50 is cold drawn type 304 stainless steel, 0.010 in thickness. Total axial length of the annulus including tabs is around 0.24 inches. Clearance between the outside diameter of annulus body 54 and syringe bore 14 is 0.000 to 0.005 inches.

Figure 3:
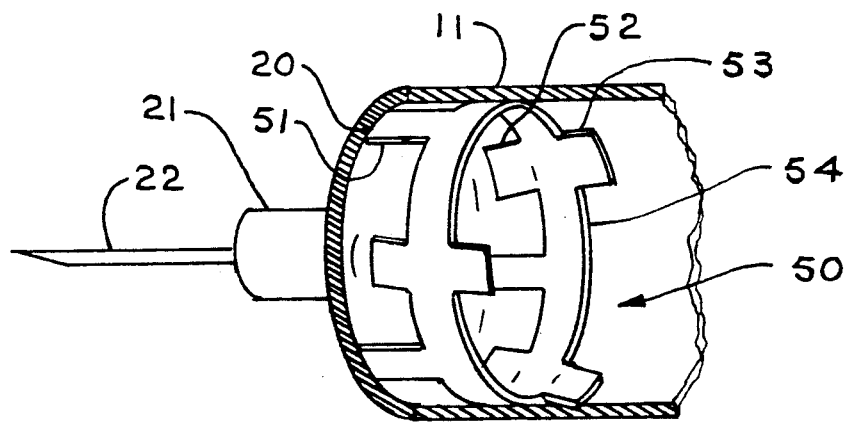
FIG. 3 sets forth a partially sectioned view of the present invention with the annulus in place in the distal end of the syringe barrel.

As shown in FIG. 3, an integral part of annulus 50 and extending in the distal direction are three locating tabs 51 spaced radially at equal distances and in contact with funnel end 20 of syringe bore 14. Locating tabs 51 are parallel to the axial centerline of the syringe and in light contact with the syringe wall. Locating tabs 51 are approximately 0.09 inches in width and 0.12 in axial length.

An integral part of annulus 50 and spaced equally between locating tabs 51 and extending in the distal direction are three locking tabs 52 of 0.06 inches in axial length and 0.09 in width which are angled inward toward the axial centerline of the syringe at a 15° angle. The distal ends 57 of locking tabs 52 are at a distance from the distal ends of locating tabs 51 slightly greater than the axial length of sealing lobe 42 of piston 40. This distance is approximately 0.06 inches.

Facing in the proximal direction and axially in line with locking tabs 52 are three anchoring tabs 53 of approximately 0.05 inches in axial length and around 0.09 inches in width. Anchoring tabs 53 are angled outward from syringe axial centerline at a 7° angle, thus bringing them in spring tight contact with the syringe bore 14. Annulus body 54 of which all tabs are an integral part is approximately 0.07 in axial length. The total axial length of annulus 50, including tabs, is around 0.24 inches.

The function of annulus 50 is as follows: when an injection is completed, piston 40 passes over annulus 50 to funnel end 20. As piston 40 passes over annulus 50, the locking tabs 52 will bend down some and sealing lobe 42 will deform some, allowing sealing lobe 42 to pass over the locking tabs. The piston is of such dimension and design that sealing lobe 41 is in full contact with the syringe wall 14 at all times, preventing fluid leakage from escaping past piston 40. Once piston 40 reaches funnel end 20, it cannot be withdrawn because the front edges of locking tabs 52 now dig into elastic piston 40. Any attempt to move locking tabs 52 in the proximal direction is prevented because anchoring tabs 53 dig into the plastic syringe wall 14 and prevent proximal movement. Since all tabs are part of annulus 50 and locking tabs 52 and anchoring tabs 53 are axially aligned and opposed on annulus 50, they effectively lock piston 20 in place at the distal end of syringe barrel 14.

Figure 4:
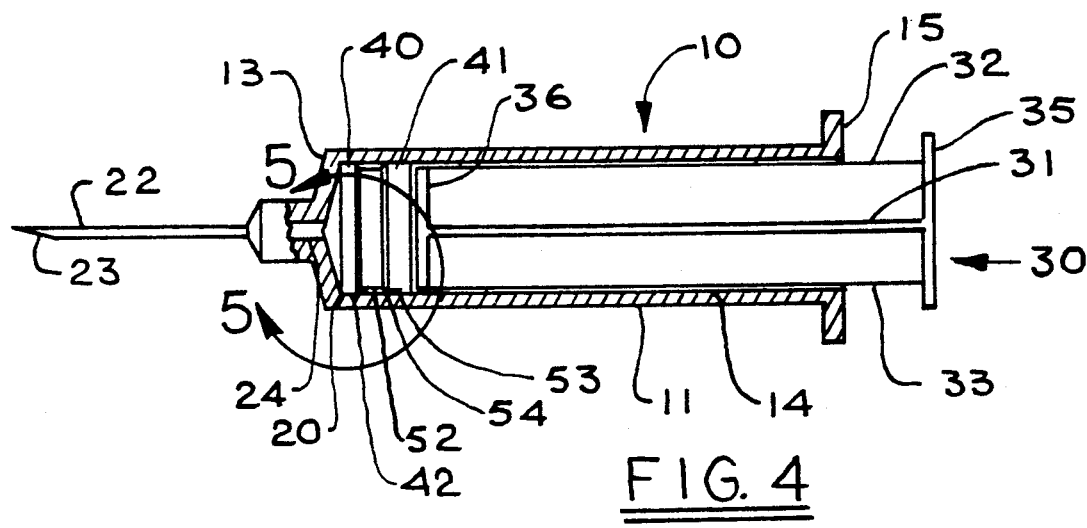
FIG. 4 sets forth a partially sectioned side view of the present invention hypodermic syringe in the locked position after delivering an injection.

FIG. 4 is a partial section view of hypodermic syringe 10 shown in the closed position after giving an injection.

Figure 5:
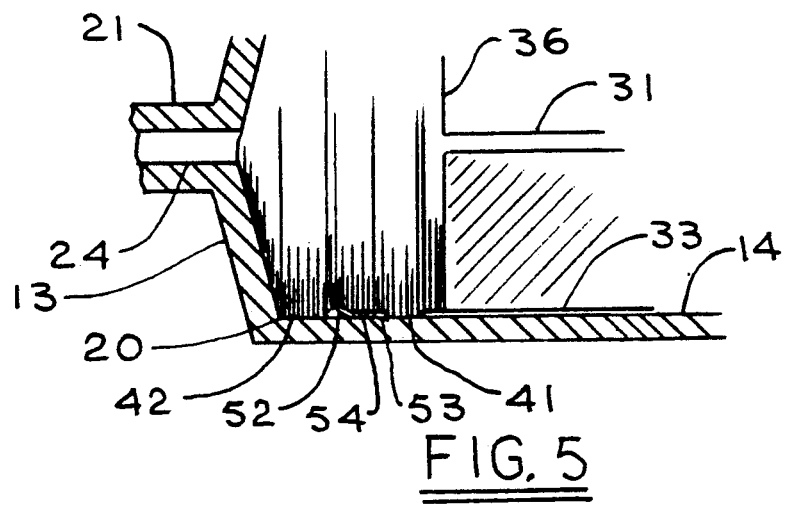
FIG. 5 sets forth an enlarged section view of the present invention taken along section line 5—5 showing the piston engaged by the annulus.

FIG. 5 sets forth an enlarged view of the distal end of syringe bore 14 taken along section line 5—5. Once piston 40 reaches funnel end 20, it cannot be withdrawn because the front edges of locking tabs 52 now dig into elastic piston 40 behind lobe 42. Any atttempt to move locking tabs 52 in the proximal direction is prevented because anchoring tabs 53 dig into the plastic syringe bore 14 and prevent movement. Since all tabs are part of annulus 50 and locking tabs 52 and anchoring tabs 53 are axially aligned and opposed on annulus 50, they effectively lock piston 40 in place at the distal end of the syringe barrel.

OPERATION

In operation, syringe 10 is delivered in a sterile package with piston 40 located in the partially opened position, approximately ⅜ inch away from funnel end 20. Annulus 50 is in place against funnel end 20 and in front of piston 40.

Figure 6:
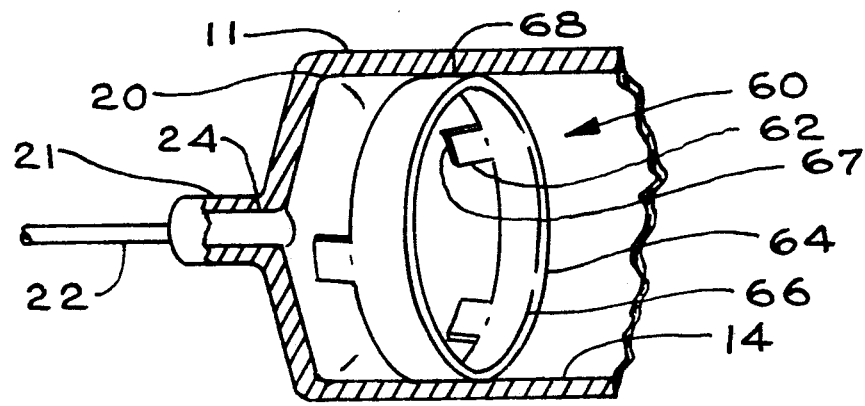
FIG. 6 sets forth a partial section view of an alternate embodiment of the present invention showing the annulus bonded in place within the syringe barrel.

Syringe 10 is removed from the package and needle 22 is inserted into a medicine vial. Pulling back on gripping flange 35 of piston driver 30 draws liquid from the vial through the needle and into the syringe. When it appears that more than enough fluid for the prescribed injection has been drawn into the syringe, piston 40 is cycled back and forth to drive any air out of syringe body 11 and into the vial. Piston 40 and piston driver 30 may be cycled in and out as often as desired as long as any part of sealing lobe 42 does not pass across locking tab 52. Excess medicine is driven back into the vial and piston 40 is stopped at the point where the desired amount of medicine is in front of it. The needle is withdrawn from the vial and the injection given to the patient, pushing the rubber piston 40 to the funnel end 20, exhausting all of the medicine. At this point it is locked in place and cannot be used again. FIG. 6 sets forth a partial section view of an alternate embodiment of the present invention showing annulus 60 bonded in place at a location near funnel end 20 of syringe bore 14. Bonding in this position eliminates the need for the anchoring tabs of the preferred embodiment of FIG. 2. Three locking tabs 62 extend in the distal direction from annulus body 64 for 0.06 inches in axial length and are angled at 15° toward the axial centerline of syringe 10. The distal ends 67 of locking tabs 62 are located at a distance from funnel end 20 of syringe bore 14 slightly greater than the axial length of sealing lobe 42 of piston 40. This distance is approximately 0.06 inches. Annulus 60 is bonded, cemented or sonic welded to syringe bore 14 at this location. In this fixed location, it permits sealing lobe 42 of piston 40 to pass over locking tabs 62 when moving in the distal direction but prevents its moving in the proximal direction when the locking tabs 62 embed themselves in sealing lobe 42. At 66, annulus is rounded or angled to permit piston 40 to pass over it smoothly.

Figure 7:
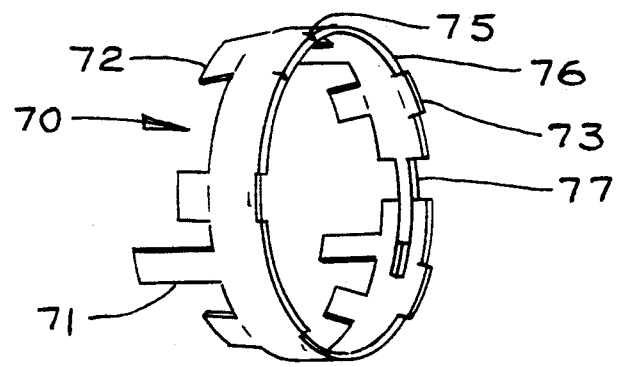
FIG. 7 sets forth a view of an alternate embodiment of the present invention annulus incorporating expansion/contraction means for adapting to varying dimensions of the syringe barrel. Also shown is an alternate embodiment of the anchoring tabs of the annulus.

FIG. 7 sets forth an alternate embodiment of annulus 70, wherein expansion/contraction joint 77 is incorporated in the body 76 of annulus 70, permitting it to increase or decrease in diameter to accomodate variations in diameter of syringe bore 14. Since syringe body 11 is molded plastic, syringe bore 14 is often slightly tapered making for a variation in diameter from the proximate end to the distal end at funnel end 20. Some models of hypodermic syringe 10 incorporate a ridge near the proximate end of syringe bore 14, and the ability of the alternate embodiment of annulus 70 to vary in diameter permits it to adapt to these variations and still maintain close contact with syringe bore 14 when located in its final position.

Also shown in FIG. 7 are five locking tabs 72, which exemplifies the fact that their quantity may be varied. Also shown is a variation of the anchoring tabs 73 wherein they are merely outward extending sections of annulus body 76 which dig into syringe bore 14, preventing movement of annulus 70 in the proximal direction. Three locating tabs 71 are shown.

Figures 8, 9:
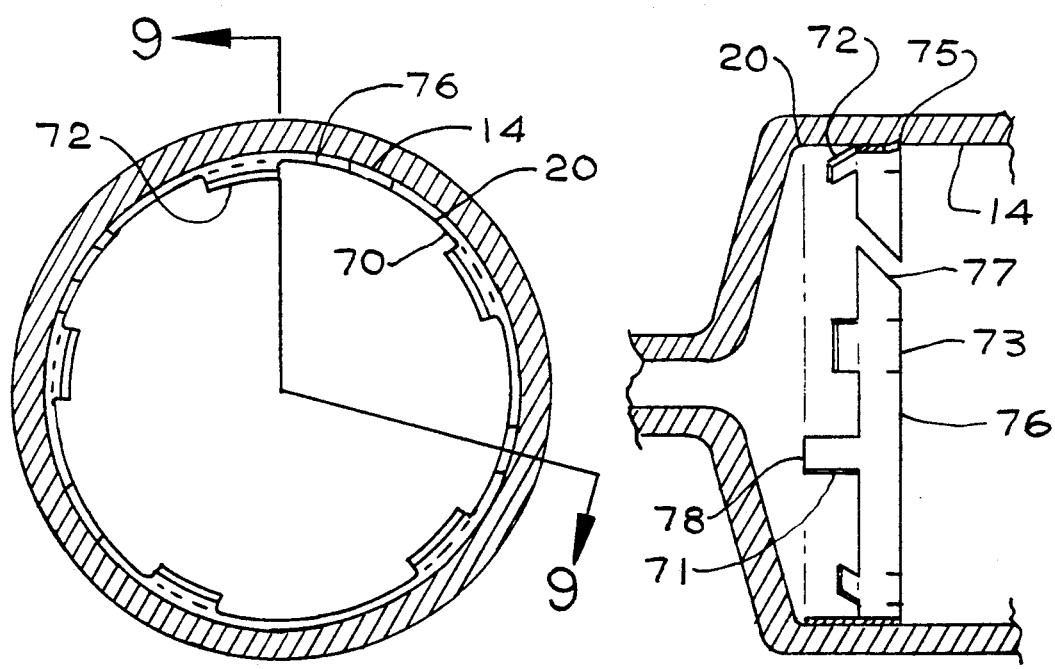
FIG. 8 sets forth a partial section view looking in the proximal direction from the distal end of the present invention hypodermic syringe barrel, showing an annulus with five locking tabs in position in the syringe barrel.
FIG. 9 sets forth a partial section view of the distal end of the present invention hypodermic syringe barrel taken along section line 9—9 showing a type of expansion/contraction means.

FIG. 8 sets forth a partial section end view of syringe body 14 looking in the proximal direction from funnel end 20. Annulus 70 is shown in contact with syringe bore 14. Locking tabs 72 are shown extending inwardly toward the axial centerline of syringe bore 14.

FIG. 9 sets forth a partial section view taken along section line 9—9. Distal end 78 of locating tabs 71 are shown against funnel end 20 of syringe bore 14. Locking tabs 72 are shown at a distance of approximately 0.06 inches in the proximal direction from distal end 78 of locating tab 71. Expansion/contraction joint 78 is shown in its median position. Anchoring tabs 73 are shown as outwardly extending sections of annulus body 76 and dig into syringe bore 14 at 75 when movement in the proximal direction is attempted.

Figure 10:
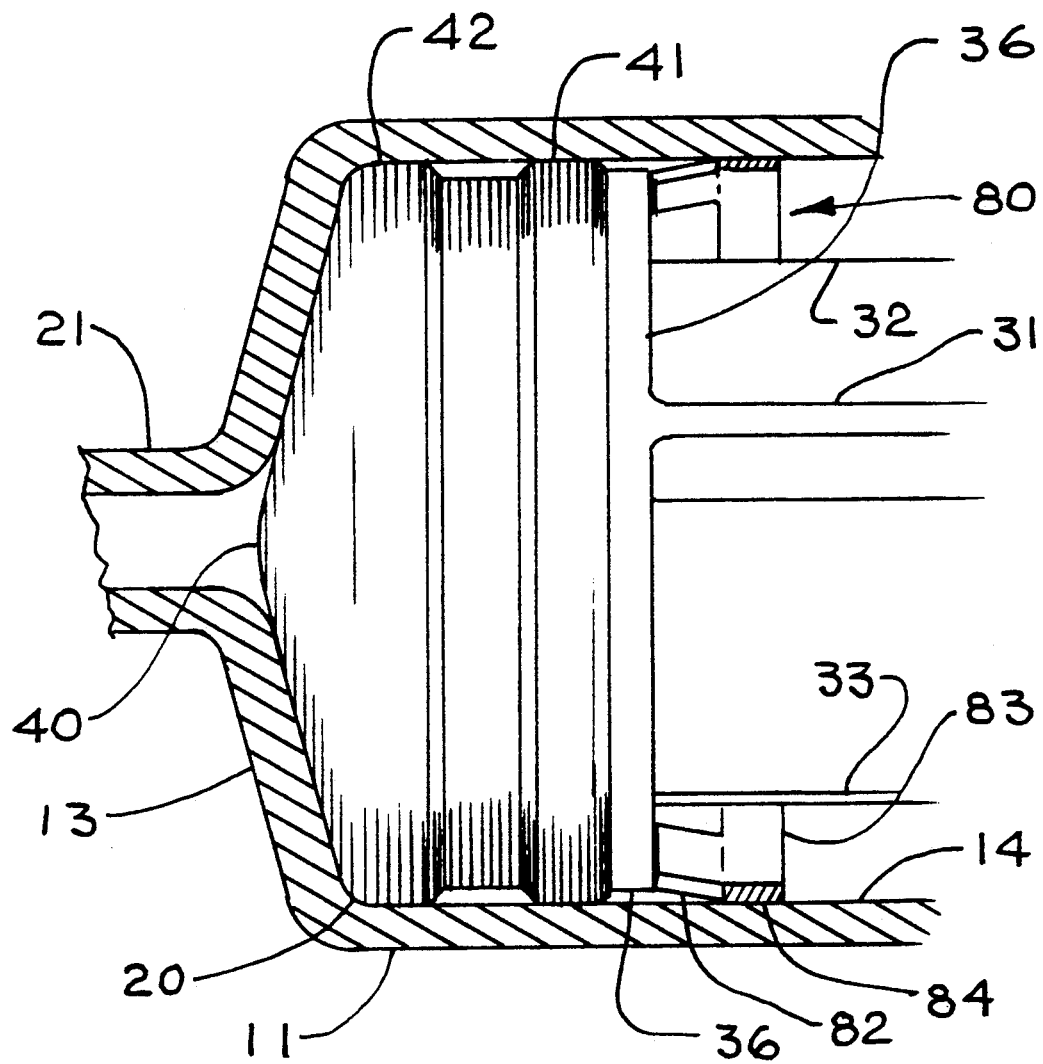
FIG. 10 sets forth a partial section view of an alternate embodiment of the present invention showing the annulus locking against the piston pushing flange of the piston driver.

FIG. 10 sets forth an alternate embodiment of the present invention whereby annulus 80 is located at a position from funnel end 20 such that locking tabs 82 will lock behind piston pushing flange 36 of piston driver 30 when piston 40 is moved to funnel end 20 of syringe bore 14 at the completion of giving an injection. Annulus 83 is bonded to syringe bore 14 at 84.

In each of the embodiments shown, the annulus is located within a hypodermic syringe in a position where, when the injection is completed, the piston driver is locked in the closed position and cannot be withdrawn to be used to give another injection.

While particular embodiments of the invention have been shown and described, it will be obvious to those skilled in the art that changes and modifications may be made without departing from the invention in its broader aspects. For example, it is obvious that sharp points could be incorporated in the faces of both locking tabs and anchoring tabs in order to engage the piston and barrel wall more readily. It is also obvious that other edges could be rounded and/or angled to make the passage of the piston in the distal direction easier.

Therefore the aim in the appended claims is to cover all such changes and modifications as fall within the true spirit and scope of the invention.

What is claimed is:

1. A single use syringe assembly having misuse resistant features comprising;
   a. a barrel having an inside surface describing a chamber for retaining fluid, said barrel having an open barrel end and a distal barrel end having a passageway therethrough in fluid communication with said chamber;
   b. a piston driver including an elongate body portion having a proximal end and a distal end, said distal end being attached to an elastic piston, said piston being slidably positioned in fluid tight engagement in said barrel, said body portion of said piston driver extending proximally from said open barrel end;
   c. an annulus fixedly placed within said barrel, with one or more integral projections thereon facing in the distal direction, the front face of said projections located at a distance equal to 5 percent to 100 percent of the axial length of said piston from said distal barrel end, said projections being angled inward toward the axial centerline of said syringe at an angle between 1° and 45° which will permit all or part of said piston to pass said projections when said piston is being advanced in the distal direction to said distal barrel end, but when said piston driver is subsequently urged in the proximal direction, said projections engage the piston, preventing proximal movement;
   d. Said annulus contains one or more integral proximally facing projections which are angled outwardly from the axial centerline of said syringe at 1° to 30° which brings them into contact with said inside surface of said barrel, permitting said annulus to slide across said inside surface of said barrel when it is urged in a distal direction but when said annulus is urged in a proximal direction, said projections engage said inside surface of said barrel, preventing proximal movement of the annulus.

2. The syringe assembly of claim 1 wherein said annulus is positioned and affixed against distal motion by one or more distally facing projections which abut said barrel end.

3. The syringe assembly of claim 1 wherein said annulus is affixed to said barrel inside surface by bonding means.

4. The syringe assembly of claim 1 wherein said annulus is composed of corrosion resistant metal.

5. The syringe assembly of claim 4 wherein said corrosion resistant metal is 0.020 inches or less in thickness.

6. The syringe assembly of claim 1 wherein said annulus is composed of plastic.

7. The syringe assembly of claim 1 wherein said annulus has means wherein it can expand or contract in diameter for adapting to variations in the diameter of said barrel inside surface.

8. A single use syringe assembly having misuse resistant features comprising;
   a. A barrel having an inside surface describing a chamber for retaining fluid, said barrel having an open barrel end and a distal barrel end having a passageway therethrough in fluid communication with said chamber;
   b. a piston driver including an elongate body portion having a proximal end and a distal end, said distal end being attached to an elastic piston, said piston driver body including a pushing flange adjacent said piston, said piston being slidably positioned in fluid tight engagement in said barrel, said body portion of said piston driver extending proximally from said open barrel end;
   c. an annulus fixedly placed within said barrel, with one or more integral projections thereon facing in the distal direction, the front face of said projections located at a distance exceeding the length of the piston plus the length of the piston pushing flange of the piston driver from the distal end of said barrel inside surface, said projections being angled inward toward the axial centerline of said syringe at an angle between 1° and 45° which will permit said piston and said pushing flange to pass said projections when said piston is being advanced in the distal direction to said distal barrel end, but when said piston driver is susequently urged in the proximal direction, said projections engage the piston pushing flange, preventing its proximal movement;
   d. said annulus is positioned and affixed against proximal motion by one or more integral proximally facing projections which are angled outwardly from the axial centerline of said syringe at 1° to 30° which brings them into contact with said inside surface of said barrel, permitting said annulus to slide across said inside surface of said barrel when it is urged in a distal direction but when said annulus is urged in a proximal direction, said projections engage said inside surface of said barrel, preventing proximal movement of the annulus.

9. The syringe assembly of claim 8 wherein said annulus is positioned and affixed against distal motion by one or more distally facing projections which abut said barrel end.

10. The syringe assembly of claim 8 wherein said annulus is affixed to said barrel inside surface by bonding means.

11. The syringe assembly of claim 8 wherein said annulus is composed of a corrosion resistant metal.

12. The syringe assembly of claim 11 wherein said corrosion resistant metal is 0.020 inches or less in thickness.

13. The syringe assembly of claim 8 wherein said annulus is composed of plastic.

14. The syringe assembly of claim 8 wherein said annulus has means wherein it can expand or contract in diameter for adapting to variations in the diameter of said barrel inside surface.

* * * * *